United States Patent [19]

Haynes

[11] Patent Number: 5,131,403
[45] Date of Patent: Jul. 21, 1992

[54] METHOD FOR OBTAINING BLOOD USING IONTOPHORESIS

[75] Inventor: John L. Haynes, Chapel Hill, N.C.

[73] Assignee: Becton Dickinson and Company, Franklin Lakes, N.J.

[21] Appl. No.: 710,420

[22] Filed: Jun. 5, 1991

[51] Int. Cl.$^5$ ................................................ A61B 5/00
[52] U.S. Cl. ...................................... 128/760; 604/20
[58] Field of Search ............... 128/760, 762, 763, 765, 128/768, 770; 604/20, 21, 51

[56] References Cited

U.S. PATENT DOCUMENTS

| | | | |
|---|---|---|---|
| 3,991,755 | 11/1976 | Vernon et al. | 604/20 |
| 4,411,648 | 10/1983 | Davis et al. | 604/21 |
| 4,474,570 | 10/1984 | Ariura et al. | 604/20 |
| 4,569,673 | 2/1986 | Tesi | 604/20 |
| 4,764,164 | 8/1988 | Sasaki | 604/20 |
| 4,978,446 | 12/1990 | Lobdell | 210/206 |
| 5,015,228 | 5/1991 | Columbus et al. | 604/51 |
| 5,019,034 | 5/1991 | Weaver et al. | 604/20 |
| 5,023,085 | 6/1991 | Francoeur et al. | 424/449 |

FOREIGN PATENT DOCUMENTS 8930191 9/1989 European Pat. Off. .

OTHER PUBLICATIONS

D. Bates et al., JAMA 265:363 (1991), "Contaminant Blood Cultures . . . ".
R. O. Becker et al., *The Journal of Bone and Joint Surgery* 60-A:871 (1978) "Treatment of Orthopaedic Infections . . . ".

*Primary Examiner*—Max Hindenburg
*Assistant Examiner*—Guy V. Tucker
*Attorney, Agent, or Firm*—Brian K. Stierwalt

[57] ABSTRACT

The present invention provides a method for obtaining blood from a patient which comprises:
 (a) iontophoretic delivery of a bacteriocidal effective amount of a bacteriocide through the patient's skin, and
 (b) obtaining blood through the skin at the site of the iontophoretic delivery.

The invention is particularly advantages in reducing the effects of contaminants responsible for large numbers of false positives. This advantageous is beneficial not only to a patient who benefits from an accurate diagnosis, but is also beneficial economically by eliminating unnecessary hospital stays, testing, and consulting.

14 Claims, No Drawings

METHOD FOR OBTAINING BLOOD USING IONTOPHORESIS

FIELD OF THE INVENTION

The invention is the field of blood culturing. In particular, the invention is in the area of obtaining blood.

BACKGROUND

Contaminant blood cultures are common, representing up to half of all positive blood cultures. D. Bates et al., *JAMA* 265:363 (1991). Contaminants can in turn lead to unnecessary therapy, such as the administration of antibiotics, and additional testing and consulting. In addition, contaminated blood cultures can result in unnecessarily prolonged hospital stays. Such unnecessary procedures result in excess laboratory fees, diagnostic fees, pharmacy fees, physicians' fees, and hospital fees. Thus, in addition to inconvenience and potential harm to a patient, the true costs associated with contaminated blood cultures can be economically exorbitant.

The increased costs associated with contaminated blood cultures underscores the importance of sterile technique when obtaining blood samples.

Although the importance of sterile technique in the medical field, and in the area of blood sampling and culturing in particular has been known for some time, evidence as presented in the study by D. Bates et al. demonstrates a continued and urgent need for improvements in sterile techniques.

Recent activity in the area of sterile techniques is evidenced in European Patent Application number 89301916.6 directed to anesthesia and antisepsis of the skin. In the European application the use of transdermal delivery of anesthetics having antimicrobial properties is disclosed.

However, the need for sterile techniques for obtaining blood free of contaminants is still unmet.

SUMMARY OF THE INVENTION

The present invention provides a sterile technique for obtaining blood. The invention is a method for obtaining blood from a patient which comprises (a) iontophoretic delivery of a bacteriocidal effective amount of a bacteriocide through the patient's skin, and (b) obtaining blood through the skin at the site of the iontophoretic delivery Further embodiments of the invention include the iontophoretic delivery of anesthetics, enhancers, and the like along with the bacteriocide.

Other embodiments of the invention include the topical administration of anesthetics, enhancers, and the like prior to the delivery of a bacteriocide.

Preferred embodiments include the iontophoretic delivery of anesthetics as bacteriocides and the iontophoretic delivery of silver as a bacteriocide.

The invention is particularly advantageous in that it provides both a sterile technique and an essentially bacteria free blood sample, which eliminates the problems associated with contamination, and a rapid sterilization of the area from which the blood sample is to be obtained. By obtaining sterile blood samples, erroneous additional testing, consulting, hospital stays, and exorbitant costs associated therewith are eliminated. The ability to obtain a sterile blood sample is particularly advantageous when a culture will be necessary. In addition, patients are afforded better and quicker diagnosis, which value includes greater peace of mind to all those involved.

As used in this document, "patient" refers to animals, including humans, household animals such as dogs and cats, livestock such as cattle, horses, sheep, pigs, goats and rabbits, laboratory animals such as mice and rats, and zoo animals such as exotic species. "Bacteriocide" refers to any composition comprising an agent suitable for administration to a patient which is effective in substantially reducing the effects from bacteria, which effects will no longer create false positives to the point of interfering with sample interpretation. "Bacteriocidal effective amount", as used in this document, refers to that amount which results in a substantial reduction in the effect of bacteria contaminants in a blood sample, the primary effect being a reduction in false positives.

DETAILED DESCRIPTION OF THE INVENTION

Blood collection techniques are routine for most hospital and physician personnel. Reference manuals on the practice and handling of laboratory specimens include J. Slockbower and T. Blumenfeld, "Collection and Handling of Laboratory Specimens," (J. P. Lippincott Company, Phila., Pa., 1983) and F. Fischbach "A manual of laboratory diagnostic tests, third edition" (J. P. Lippincott Company, Phila., Pa., 1988).

Blood collection means for withdrawing blood include collection tubes such as test tubes and capillary tubes, and needle and syringe means such as evacuated blood collection means such as a VACUTAINER system.

The particular locale for obtaining a blood sample will depend on a variety of factors such as the amount of sample needed and the specifics of the individual. For example, blood typing or a crude cholesterol reading may require only a few drops of blood easily obtainable with a finger stick. However, a complete blood analysis may require several milliliters, most easily obtainable by venipuncture, for example, puncture of the antecubital vein. Sterility is most desired when a sample of blood is to be cultured. The preferred locale for obtaining blood samples from an infant is usually the heel or earlobe, while the preferred locale for an adult might be the arm or leg. The professional in charge of obtaining the blood sample is generally knowledgeable of the proper locale and proper amounts necessary for a particular need.

The typical protocols for preparing patients for obtaining blood samples can be used in conjunction with the present invention. For example, the use of alcohols, povidone-iodine (Betadine), and warming.

Once the amount of blood sample to be obtained is known and once the locale for obtaining the blood sample is chosen, the present invention can be practiced.

There are a variety of iontophoretic devices which can be used to practice the invention. The particular device employed is not key. However, the ability to deliver a bacteriocide to the locale, both to the surface and into the skin, from which a blood sample is to be obtained is key. Generally, iontophoretic devices comprise at least two electrodes, an electrical energy source (e.g., a battery) and at least one reservoir which contains a composition to be delivered. Several iontophoretic devices are known, such as those disclosed in P. Tyle, *Pharmaceutical Biosearch* 3:318 (1986). Several recent United States patents describe iontophoretic devices such as J. Phipps et al. in U.S. Pat. No. 4,744,787 and D. Sibalis in U.S. Pat. No. 4,808,152.

The iontophoretic delivery of bacteriocides has several advantages. In particular, speed is greatly enhanced over topical or passive transdermal delivery methods. Depth of penetration is also enhanced and attained in less time than topical or passive transdermal delivery methods. The ability to obtain a rapid bacteriocidal effect is especially beneficial due to the fact that the inconvenience and discomfort associated with longer delivery methods, such as wearing a patch, is eliminated. The ability to achieve bacteriocidal effect within the skin (i.e., depth) is also advantageous due to the fact that common bacteria contaminants exist within the skin and are not always effected by non-iontophoretic delivery methods.

A variety of bacteriocides can be used to practice the present invention. Suitable bacteriocides include known anesthetics. Anesthetics that have antimicrobial properties are preferred bacteriocides for use in practicing the invention. Procaine and lidocaine are two anesthetics that have both antimicrobial and anesthetic properties.

Bacteriocides also include iodine compounds such as solutions of free Iodine (e.g., iodide in water, ethyl alcohol, and the like), iodophors, quarternary ammonium compounds such as Benzalkonium chloride and cetyltrimethyl ammonium bromide, chlorhexidine gluconate, and acetyl salicylic acid (i.e., aspirin).

Preferred characteristics of bacteriocides for iontophoretic delivery include proper ionic form, minimal toxicity to the patient, minimal irritation to the patient, ease of skin penetration (e.g., molecular weight), good water solubility, quick action, and broad spectrum.

Silver is also a known bacteriocide that can be used in the present invention. The bacteriocidal properties of silver have been known for some time. Free silver ions, as are used in iontophoretic delivery, due to their small size, can penetrate virtually any structure that has an aqueous component. Since silver ions are continuously released from the electrode (e.g., anode) the amount of silver delivered into the skin and beneath the skin is generally in excess of that necessary for obtaining a bacteriocidal effective amount. Even though excess silver may be delivered, silver is only minimally toxic and the amount typically delivered by iontophoresis is far below any amount necessary to produce a detectable body burden.

Although the delivery of a bacteriocide to the locale from which a blood sample is to be obtained is responsible for obtaining essentially contaminant free blood samples, other substances can be iontophoretically delivered along with the bacteriocide. For example, if the bacteriocide is not an anesthetic, anesthetic can be iontophoretically delivered with the bacteriocide to help alleviate any pain or discomfort that may be associated with obtaining blood. Suitable anesthetics include benzocaine, procaine, lidocaine, ropivacaine, etidocaine, bupivacaine, tetracaine, prilocaine, the salt forms of anesthetics, and mixtures thereof. Likewise, known enhancers for increasing penetration can be delivered along with the bacteriocide, anesthetic, or both. Enhancer compounds known for promoting diffusion of substances through the skin include dimethly lauramide, 1-dodecylazocycloheptan-2-one, glycerol dimethyl ketal, isopropyl myristate, and N,N-diethyl-toluamide. *J. Pharm. Sci.*, 71:1211 (1982).

Drug modification (e.g., anesthetics), if necessary for ionotophoretic delivery, is guided by well-known procedures. For example, to deliver a positively charged drug, the chloride or hydrochloride form of the drug can be made and placed in the iontophoretic device reservoir for delivery. General texts in the field include Remington's Pharmaceutical Sciences, Ed. Arthur Osol, 16th ed., 1980, Mack Publishing Co., Easton, Pa. Typically, the basic ($OH^-$ or amine) or acidic ($H^+$) form of the drug is made, depending on whether the anionic (negative charged ion) or cationic (positive charged ion) form of the drug is to be delivered. Common modifications include modification to a halide salt form. For example, to deliver a positively charged drug, the chloride or hydrochloride form of the drug is made and placed in the iontophoretic device reservoir for delivery. Likewise, the composition is typically dissolved in a suitable solvent to obtain the ionic form for iontophoretic delivery. Suitable solvents include polar liquids such as water, glycerine, and lower alkyl alcohols such as methyl alcohol, ethyl alcohol, and branched alcohols such as isopropyl alcohol.

In addition to iontophoretic delivery, anesthetics, enhancers, and the like, can be administered topically. Subsequent practice of the invention can then be employed.

After the bacteriocide has been delivered to the surface and into the skin, a sample of blood can be withdrawn. Since the locale from which the blood sample to be obtained has been treated with a bacteriocide, essentially no bacterial contaminants from the skin (e.g., on the surface or within) will enter the withdrawn blood. This is particularly advantageous since most sterile techniques involving blood samples introduce contaminants from or within the skin into the obtained blood sample. It is the introduction of contaminants at this point in most blood sample collection techniques that is responsible for the contamination problems providing the high number of false positives. Typical normal flora of skin which are common contaminants responsible for false positive blood cultures include *Staphylococcus aureus* and *Staphylococcus epidermidis*. H. L. Moffet, "Clinical Microbiology, second edition", (J. B. Lippincott Company, Phila., Pa., 1980). However, all gram-negative and gram-positive bacteria are generally susceptible to the bacteriocidal effects of silver. This is also advantageous since not all antibiotics and bacteriocides are effective for the same range of bacteria. In addition, since the typical blood collection means involves such a small invasion into the skin, the iontophoretically delivered silver is especially effective. There is no need for the silver to be effective over a wide area of skin.

By practicing the present invention, the iontophoretic delivery of a bacteriocidal effect amount of a bacteriocide substantially eliminates the contaminants responsible for providing the large numbers of false positives.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A method for obtaining blood from a patient which comprises:
    (a) iontophoretic delivery of a bacteriocidal effective amount of a bacteriocide through the patient's skin, and (b) obtaining blood through the skin at the site of said iontophoretic delivery.

2. The method of claim 1 in which the obtaining step is performed by the blood collection means selected from the group consisting of test tubes, capillary tubes, needle and syringe, and evacuated collection means.

3. The method of claim 2 in which the means to collect blood is by needle and syringe.

4. The method of claim 2 in which the means to collect blood is by evacuated collection means.

5. The method of claim 1 in which the site of said iontophoretic delivery is pretreated with a composition selected from the group consisting of enhancers and anesthetics.

6. The method of claim 5 in which the composition is an enhancer.

7. The method of claim 5 in which the composition is an anesthetic.

8. The method of claim 1 in which the bacteriocide is selected from the group consisting of anesthetics, silver, iodine compounds, iodophors, quarternary ammonium compounds, and acetyl salicylic acid.

9. The method of claim 8 in which the bacteriocide is an anesthetic.

10. The method of claim 9 in which the anesthetic is selected from the group consisting of benzocaine, procaine, lidocaine, ropivacaine, etidocaine, bupivocaine, tetracaine, prilocaine, salt forms, and mixtures thereof.

11. The method of claim 10 in which the anesthetic is lidocaine.

12. The method of claim 10 in which the anesthetic is procaine.

13. The method of claim 10 in which the anesthetic is ropivacaine.

14. The method of claim 8 in which the bacteriocide is silver.

* * * * *